United States Patent [19]

Ishibashi

[11] Patent Number: 5,087,423
[45] Date of Patent: Feb. 11, 1992

[54] AUTOMATIC ANALYZING APPARATUS COMPRISING A PLURALITY OF ANALYZING MODULES

[75] Inventor: Kiyochika Ishibashi, Kokubunji, Japan

[73] Assignee: Olympus Optical Co., Ltd., Tokyo, Japan

[21] Appl. No.: 422,597

[22] Filed: Oct. 17, 1989

[30] Foreign Application Priority Data

Oct. 20, 1988 [JP] Japan .................. 63-262982
Dec. 19, 1988 [JP] Japan .................. 63-318398

[51] Int. Cl.⁵ .................................... F01N 21/00
[52] U.S. Cl. .............................. 422/67; 422/63; 422/65
[58] Field of Search ............ 422/63, 65, 67, 64; 436/43, 47, 48

[56] References Cited

U.S. PATENT DOCUMENTS

| | | | |
|---|---|---|---|
| 3,883,305 | 5/1975 | Hoskins et al. | 422/67 |
| 3,883,306 | 5/1975 | Widen | 422/67 |
| 3,917,455 | 11/1975 | Bak et al. | 422/64 |
| 4,113,436 | 9/1978 | Werder et al. | 422/67 |
| 4,338,279 | 7/1982 | Orimo et al. | 422/65 |
| 4,512,952 | 4/1985 | Blanding et al. | 422/66 |
| 4,678,752 | 7/1987 | Thorne et al. | 422/65 |
| 4,708,886 | 11/1987 | Nelson | 422/63 |
| 4,781,891 | 11/1988 | Galle et al. | 422/64 |
| 4,805,469 | 2/1989 | Commarmot | 422/64 |

FOREIGN PATENT DOCUMENTS

| | | |
|---|---|---|
| 0317677 | 5/1989 | European Pat. Off. . |
| 2402166 | 12/1974 | Fed. Rep. of Germany . |
| 2501054 | 8/1975 | Fed. Rep. of Germany . |
| 2617944 | 5/1979 | Fed. Rep. of Germany . |
| 53-8544 | 3/1978 | Japan . |
| 2189884 | 11/1987 | United Kingdom . |

Primary Examiner—Robert J. Warden
Assistant Examiner—Theresa A. Trembley
Attorney, Agent, or Firm—Stevens, Davis, Miller & Mosher

[57] ABSTRACT

An automatic analyzing apparatus in which a plurality of analyzing modules, a plurality of analyzing routes and at least one bypass route bypassing at least one analyzing module are arranged. Each analyzing module is capable of analyzing samples with respect to one or more items, and samples successively supplied from the introduction sides of the modules are selectively delivered into each module in accordance with the possible analyzing items of each module and the analyzing items of the samples to be analyzed. The sample cup can pass the module via a bypass or can be returned to the introduction side of the module via a bypass, in accordance with the items to be analyzed, the effective distribution of the sample cups can be performed.

9 Claims, 4 Drawing Sheets

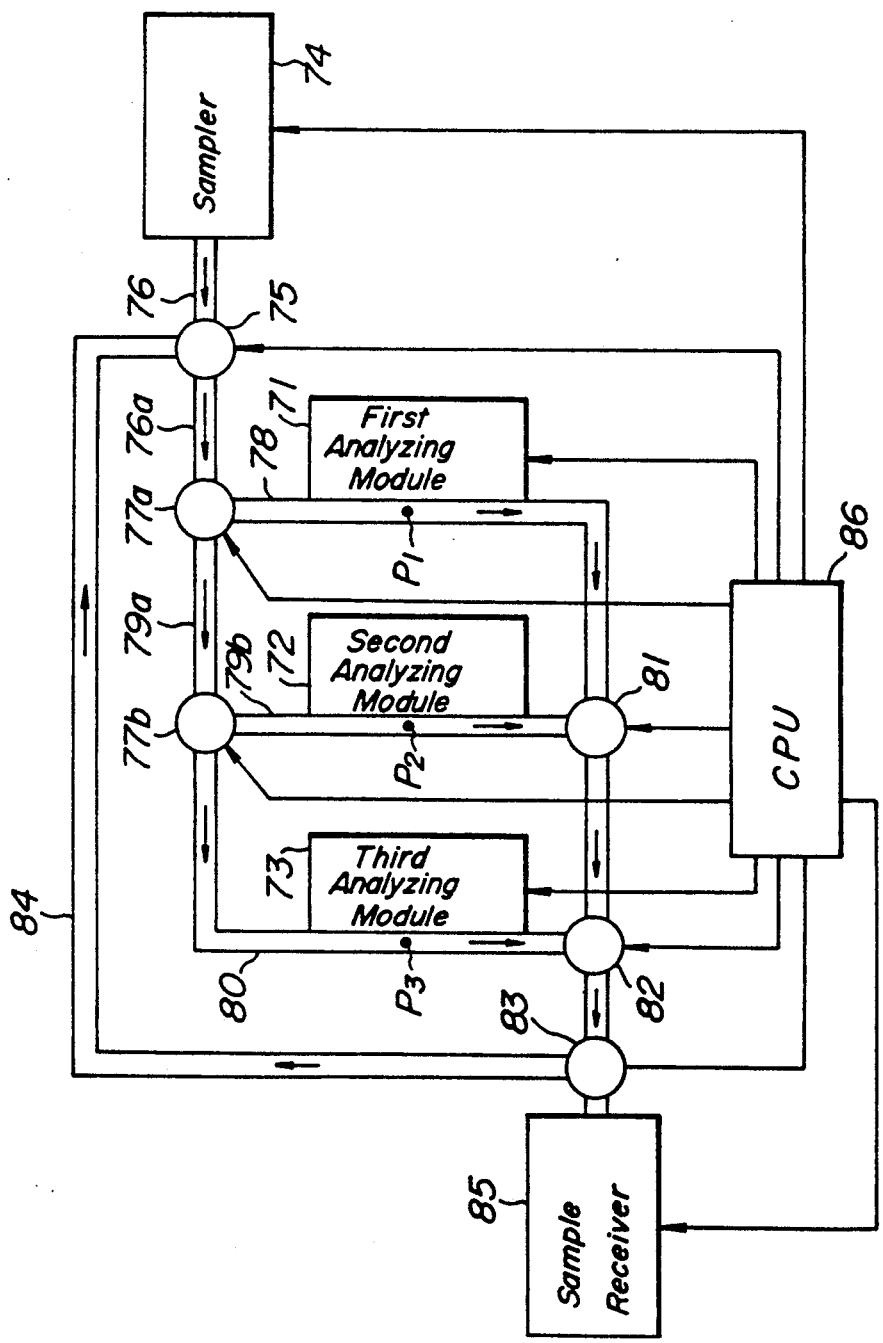

AUTOMATIC ANALYZING APPARATUS COMPRISING A PLURALITY OF ANALYZING MODULES

BACKGROUND OF THE INVENTION

1. Field of the Invention and Related Art Statement

The present invention relates to an automatic analyzing apparatus, and more particularly relates to an apparatus for chemically analyzing different kinds of substances contained in a sample liquid such as blood by means of a plurality of automatic analyzing modules each being capable of analyzing sample liquid with respect to one or more analyzing items, samples being successively fed from the upstream side of the modules and being selectively delivered into reaction vessels of the modules.

Such an automatic analyzing apparatus mentioned above is already known, for example, from Japanese Utility Model Publication Sho 53-8544. In this conventional apparatus, analyzing modules ranging from two to eight are serially arranged, and sample cups each containing sample liquids to be analyzed are successively conveyed to the modules one by one via only one route. Necessary amounts of the samples are picked up and delivered into reaction vessels in the modules in accordance with one or more analyzing items of each samples and one or more analyzing items which can be analyzed by each modules. That is to say, in the conventional apparatus, although it is not necessary to analyze all items by all analyzing modules, all samples have to be successively fed along all the analyzing modules. In the known apparatus, a conveyer belt is generally arranged to feed the sample cups along the analyzing modules. Since the number of items ranging from four to twelve can be generally analyzed in one module, it is possible to analyze 20-30 items in the automatic analyzing apparatus as a whole. On the other hand, generally, analyzing items designated for respective samples are different to each other. In general, the number of items required to be analyzed for a sample is 50-60% of all possible analyzing items of the apparatus. In order words, 50-40% of the possible items which can be analyzed by the apparatus are not designated for respective samples.

As explained above, in the conventional automatic analyzing apparatus, all sample cups are successively fed along all the analyzing modules without regard to test items designated for respective samples to be analyzed. Therefore, during a sample, whose test items are not analyzed in a module, is passing over the module, analysis is not performed in the module, thus making the processing time of the apparatus as a whole long. Particularly, in case many samples necessary to be analyzed with respect to only a few items are successively supplied into the apparatus, this disadvantage is manifested.

SUMMARY OF THE INVENTION

The present invention has for its object to provide an automatic analyzing apparatus in which the operating efficiency of the apparatus is remarkably improved. The automatic analyzing apparatus according to the present invention comprises:

sample supply means for successively supplying sample cups containing samples to be analyzed;

a plurality of analyzing modules, each of which is capable of analyzing at least one analyzing item and has a sample delivery device for delivering samples into reaction vessels;

a plurality of first routes in each intermediate portion of which one of said analyzing modules is arranged;

at least one second route bypassing at least one analyzing module; and means for controlling the delivery of said sample cups such that each sample cups supplied from said sample cup supply means are selectively delivered into either one of said first routes or said second route.

In the automatic analyzing apparatus according to the present invention, the analyzing modules may be arranged serially or in parallel and the sample cups are supplied into one of the analyzing modules in accordance with the analyzing item of the sample contained in the sample cup without respective to an order of supplying the sample cups from the sample cup supply means. In a preferred embodiment of the apparatus according to the invention first and second analyzing modules are arranged in a series manner, and there is arranged a bypass for every analyzing module in addition to a analyzing route so as to connect both up- and down-stream sides of the analyzing module via the bypass. Sample cups are supplied into either the bypass or the analyzing route in accordance with analyzing items designated to samples to be analyzed and items possible to be analyzed by the module. That is to say, if a sample does not need to be analyzed by the first analyzing module, a sample cup containing the sample can be supplied to the second analyzing module via the bypass arranged in parallel with the first analyzing route. And, if a sample is not necessary to be analyzed by the second module, a sample cup containing this sample can be fed into the down-stream side of the second analyzing module via the bypass arranged in parallel with the analyzing route of the second module after the delivery of the sample has been done in the first module.

In another preferred embodiment of the analyzing apparatus according to the invention, first and second modules are arranged in a parallel manner, and a single bypass is provided to bypass the first and second modules. In such an apparatus, the sample cups are firstly distributed to either the first module or the second module in accordance with the analyzing items of the sample to be analyzed, the items possible to be analyzed by the modules, and the occupancy of the modules by sample cups. That is to say, if a sample is to be analyzed only by the first module o the second module, the sample cup is supplied into the first module or the second module in accordance with the items. But, if a sample should be analyzed by both the first and second modules, the sample cup is first supplied into one of the first and second analyzing modules in accordance with the occupancy of the modules. Thereafter, the sample cup is returned back to the upstream side of the analyzing modules via the bypass and is supplied into the other module.

Thus, in the automatic analyzing apparatus according to the invention, it is possible to operate all of the analyzing modules efficiently without waste of time.

BRIEF DESCRIPTION OF THE DRAWINGS

FIG. 5 is a schematic view showing the structure of the fifth embodiment of the automatic analyzing apparatus according to the invention.

DETAILED DESCRIPTION OF THE PREFERRED EMBODIMENTS

Figure 1:
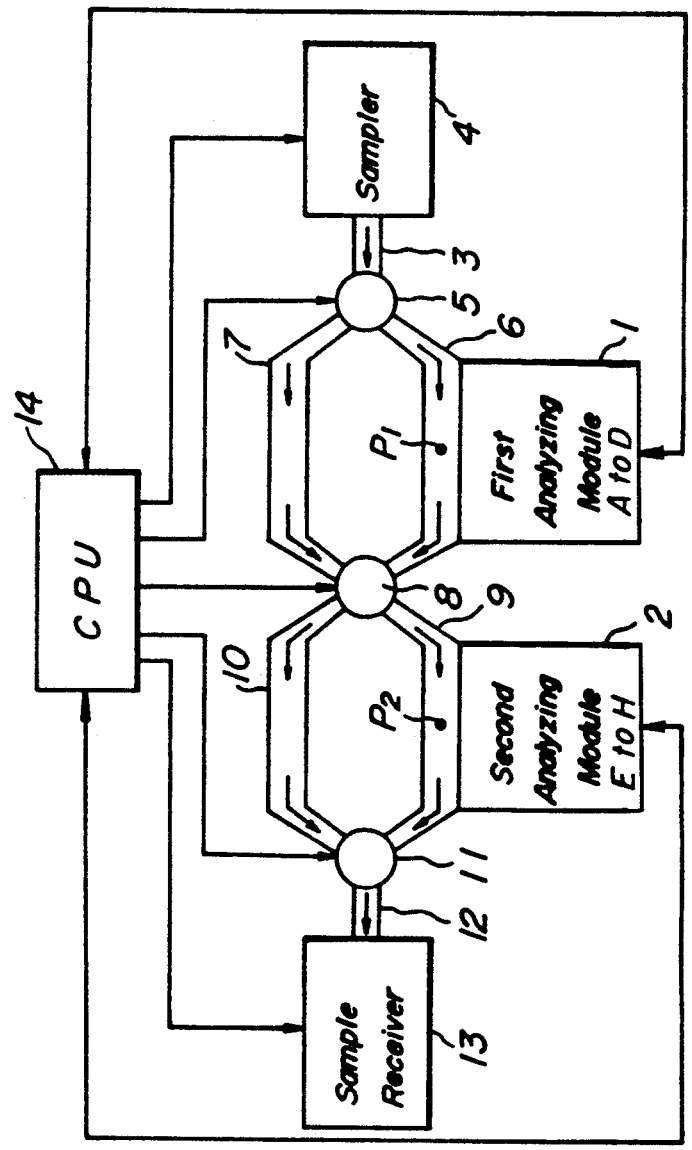
FIG. 1 is a schematic view showing the principal structure of the first embodiment of the automatic analyzing apparatus according to the invention.

FIG. 1 is a schematic view showing the principal structure of the first embodiment of the automatic analyzing apparatus according to the invention. In this embodiment, two automatic analyzing modules 1, 2 are serially arranged. The first module 1 is capable of analyzing items A to D, and the second module 2, items E to H. Each module comprises a plurality of reaction vessels and a device for delivering samples from sample cups into the reaction vessels. In the apparatus, there is arranged a sampler 4 in the upstream side of the analyzing module 1. In the sampler 4, a plurality of sample cups each containing samples to be analyzed are arranged in order and the sample cups are fed to a common route 3 one by one. The sample cups are supplied into a first sample cup distributor 5 via the common route 3. In the first distributor 5, the sample cups are distributed to a first analyzing route 6, or a first bypass 7 bypassing the first analyzing module 1 in accordance with the analyzing item of the sample contained in the sample cup. The first analyzing route 6 is connected to the first module 1 such that the sample contained in the sample cups can be delivered into the reaction vessels of the first module, and the bypass 7 is connected to a second sample cup distributor 8. That is to say, in case one or more analyzing items of the sample are to be analyzed by the first module 1, the sample cup containing the sample is distributed to the first analyzing route 6, contrary, in case one or more analyzing items of the sample ar to be analyzed by the second module 2, the sample cup is supplied into the first bypass 7, then fed to the second module 2 via the second distributor 8.

The sample cup supplied into the analyzing route 6 is stopped at a first sample picking up position $P_1$ at which part of sample contained in the sample cup is picked up by a sample picking up device (not shown) provided in the first module 1 and is delivered into the reaction vessels thereof. At the time that the analysis of the sample starts in the reaction vessel of the first module 1, the sample cup is further fed to the second sample cup distributor 8.

As stated above, the sample cup supplied into the first bypass 7 has been conveyed to the second distributor 8 and distributed to the second module 2. In the second distributor 8, the sample cups supplied from the first analyzing route 6 or the first bypass 7 are further distributed to a second analyzing route 9 or a second bypass 10 in accordance with the analyzing items of the sample. When the sample needs to be analyzed by the second module, the sample cup fed to the second analyzing route 9 and part of sample is picked up at the sample picking up position $P_2$ by a sample picking up device (not shown) provided in the second module 2 and is delivered into reaction vessels of the second module 2. At the timing that the analysis of the sample starts in the reaction vessel of the second module 2, the sample cup is conveyed to a sample cup feeder 11. On the other hand, the sample cup supplied into the second bypass 10 is also fed to the sample cup feeder 11 right away. The sample cups fed from the second analyzing route 9 and from the second bypass 10 are supplied into a sample cup receiver 13 by the sample cup feeder 11 arranged in the upstream side of the sample cup receiver 13. All operations of all devices, i.e. sampler 4, first and second sample cup distributors 5, 8, sample cup feeder 11 and sample cup receiver 13, are controlled by a central processing unit (CPU) 14 provided in the analyzing apparatus. In the CPU 14, the designated analyzing items of each sample are memorized and the positions of each sample cups in the sample cup array in the sampler 4 can be known. In order to perform the function, identification mark to be read by the CPU 14 may be provided on each sample cups or the order of the sample cups preset in the sampler 4 may be memorized in the CPU 14. The analyzing results of the analyses performed in the first and second modules 1, 2 are supplied and memorized in the CPU 14, corresponding to the identification of the sample, and are output at an appropriate timing.

Now the operation of the analyzing apparatus will be explained in the following. The items to be analyzed for samples Nos. 1-3 are shown in Table 1.

TABLE 1

| | Item | | | | | | | |
|---|---|---|---|---|---|---|---|---|
| | First analyzing module | | | | Second analyzing module | | | |
| Sample No. | A | B | C | D | E | F | G | H |
| 1 | o | | o | o | | | | |
| 2 | | | | | | o | o | |
| 3 | o | o | | | o | | | |

The samples No. 1 to No. 3 are contained in sample cups and arranged in the sampler 4 in this order. The first sample cup containing sample No. 1 is fed to the common route 3 by the sampler 4 and then conveyed to the first sample cup distributor 5. The analyzing items of the sample No. 1 are A, C and D which should be analyzed by the first analyzing module 1. Thus, the first sample cup is fed to the first analyzing route 6 and stopped at the first sample picking up position $P_1$. At the position $P_1$, a given amount of sample No. 1 is delivered into reaction vessels in the first module 1 and the items A, C and D are analyzed. During the above-mentioned operation, the second sample cup containing the sample No. 2 is supplied to the first sample cup distributor 5. Since the analyzing items F and G of the sample No. 2 are not to be analyzed by the first analyzing module 1, the second sample cup is supplied into the second sample cup distributor 8 via the first bypass 7. Since the analyzing items F and G are to be analyzed by the second analyzing module 2, the second sample cup is distributed to the second analyzing module via route 7 by the second sample cup distributor 8. The second sample cup is positioned at a sample picking-up position $P_2$ of the second analyzing module 2 and a predetermined amount of the sample No. 2 is picked-up and delivered into reaction vessels in the second module 2, and then the items F and G are analyzed. During the time that sample No. 2 is delivered into the reaction vessels in the second module 2, the delivery of the sample No. 1 has finished in the first module 1, and the first sample cup is fed to the second distributor 8. Since the analyzing items designated for the sample No. 1 do not include the analyzing items of the second module 2, the first sample cup is fed to the second bypass 10 and supplied into the sample receiver 13 right away via the sample cup feeder 11 and the common path 12. When the samples No. 1 and No. 2 have been delivered in the first and second modules 1, 2, respectively, the third sample cup containing the sample No. 3 is fed to the first sample distributor 5 from the sampler 4. Since the analyzing items of the sample No. 3 are A, B and E, the third sample cup is firstly distributed to the first analyzing route 6. The third sample cup is then stopped at the sample picking-up position $P_1$ and a given amount of the sample No. 3, which is necessary to be analyzed with respect to the items A and B, is picked-up and delivered into reaction vessels of the first module 1. By the end of the delivery operation of the sample No. 3 into the first module 1, the delivery of the sample No. 2 has been finished in the second module 2 and the second sample cup has been supplied into the sample receiver 13 via the sample feeder 11 and the common path 12.

After the delivery of the sample No. 3 has been finished in the first module with respect to the analyzing items A and B, the third sample cup is supplied into the second sample cup distributor 8. Since the sample No. 3 is designated to effect the item E in the second module 2, the third sample cup is distributed to the second analyzing route 9. The third sample cup is stopped at the sample picking-up position $P_2$ and a given amount of sample No. 3 necessary for analyzing item E is picked-up and delivered into a reaction vessel of the second module 2. After the delivery of the sample No. 3 has been finished in the second module 2, the third sample cup is supplied into the sample receiver 13 via the sample cup feeder 11 and the common path 12.

As stated above, in the first embodiment of the automatic analyzing apparatus according to the invention, since one bypass is arranged for each analyzing module, if the sample is not to be analyzed in an analyzing module, the sample cup is bypassed to the sample cup distributor positioned at the downstream side of the module through the bypass. Therefore, the waiting time of the sample cup at each analyzing module can be extremely decreased and the analyzing operation is effectively performed.

Figure 2:
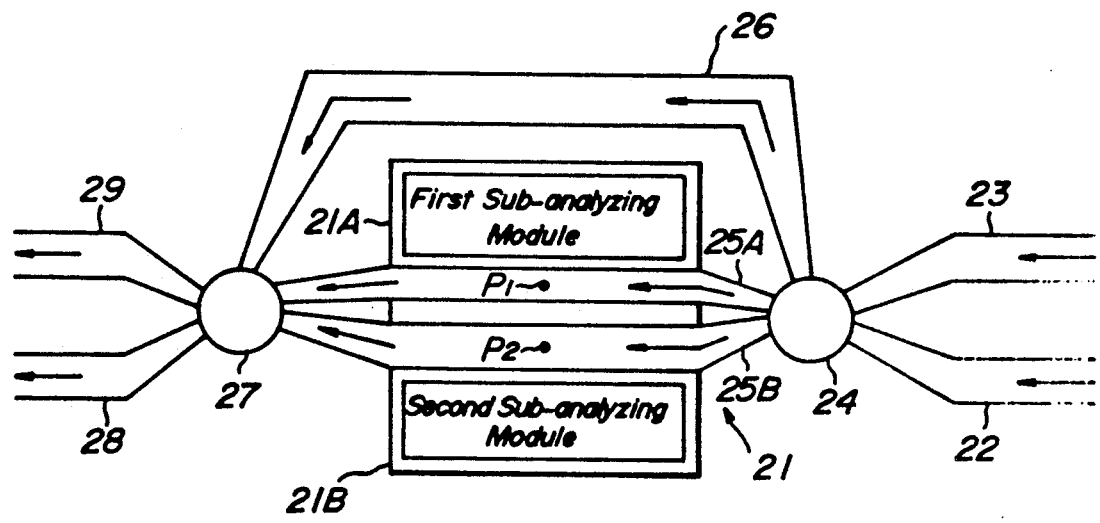
FIG. 2 is a schematic view depicting one part of the structure of the second embodiment of the automatic analyzing apparatus according to the invention.

FIG. 2 is a schematic view illustrating a major part of the structure of the second embodiment of the automatic analyzing apparatus according to the invention. In FIG. 2, there is illustrated an intermediate portion of the whole apparatus. The analyzing module 21 comprises a first sub-analyzing module 21A and a second sub-analyzing module 21B. It is possible to arrange these sub-analyzing modules 21A and 21B such that the same kind of items can be analyzed in each module, that the partially different kind of items can be analyzed in each module or that completely different items can be analyzed independently. The sample cups fed from a preceding analyzing module via an analyzing route 22 or a bypass route 23 are distributed by a distributor 24 to a first analyzing route 25A, second analyzing route 25B or a bypass 26 according to analyzing items of samples contained in sample cups. That is to say, in case the analyzing item of the sample is to be analyzed by the first sub-analyzing module 21A, the sample cup is fed to the first analyzing route 25A, and in case the analyzing item of the sample is to be analyzed by the second sub-analyzing module 21B, the sample cup is fed to the second analyzing route 25B. If the analyzing item of the sample is not to be analyzed by both the sub-analyzing modules 21A and 21B, the sample cup is fed to a succeeding module via the bypass 26. The first sample fed to the first analyzing route 25A and the second sample fed to the second analyzing route 25B are supplied into the second sample cup distributor 27 after the delivery of samples to each sub-analyzing module 21A and 21B is finished. In the second distributor 27, the sample cups fed from the analyzing routes 25A and 25B or the bypass 26 are distributed again to next analyzing route 28 or next bypass 29. As stated in the above, in case a plurality of sub-analyzing modules are arranged in one analyzing module, it is possible to arrange a plurality of analyzing routes each containing one sample picking up position. Therefore, it is possible to analyze the samples much more efficiently.

According to the first and second embodiments, a plurality of analyzing modules are serially arranged in the analyzing apparatus, and analyzing routes and bypasses are arranged to be made parallel with each other. Further, one distributor for distributing the sample cups is provided in the upstream side of each module, and the analyzing items of the sample and the items possible to be analyzed in the analyzing module are compared in the distributor. In case the analyzing items of the sample is to be analyzed by the module, the sample cup is fed to the analyzing route and in case the analyzing items of the sample is not to be analyzed by the module, the sample cup is fed to the next distributor via the bypass. Therefore, the sample cups are effectively distributed to the modules and the samples are delivered to the modules without waiting at the picking up points.

Figure 3:
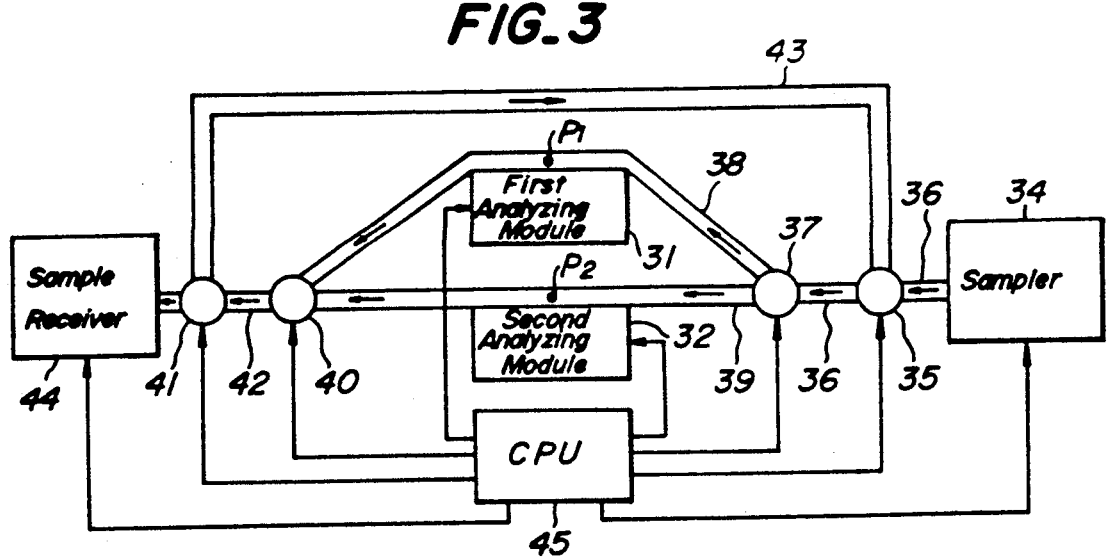
FIG. 3 is a schematic view illustrating the structure of the third embodiment of the automatic analyzing apparatus according to the invention.

FIG. 3 is a schematic view representing the structure of the third embodiment of the automatic analyzing apparatus according to the invention. In the third embodiment, a first automatic analyzing module 31 and a second automatic analyzing module 32 are parallely arranged. The first module 31 is capable of analyzing the items A-D, and the second module 32 is capable of analyzing the items E-H. In the analyzing apparatus, there is provided a sampler 34 in which a plurality of sample cups each containing samples to be analyzed are arranged in a predetermined order and these sample cups are successively fed to a common route 36 one by one by the sampler 34. The sample cup fed from the sampler 34 is supplied into a sample cup distributor 37 via a first sample cup feeder 35 and a first common route 36. In the first sample cup distributor 37, the sample cups are distributed to one of first and second analyzing routes 38, 39 in accordance with the analyzing items of the samples contained in the sample cups. That is to say, when analyzing items of a sample includes one of items which can be analyzed in the first module 31, the sample cup is distributed to the first analyzing route 38, and when all analyzing items of a sample are to be analyzed in the second module 32, the sample cup is distributed to the second analyzing route 39. And when analyzing items of a sample include analyzing items to be analyzed by both the first and second modules 31, 32, or the first analyzing route 38 connected to the first module 31 is occupied with a sample cup, the sample cup is distributed to the second analyzing route 39.

The sample cup supplied into the first analyzing route 38 is stopped at the first sample picking-up position $P_1$ of the first module 31. At the position $P_1$, part of the sample is picked-up and delivered into a reaction vessel of the first module 31. After the analysis of the sample is initiated in the reaction vessel, the sample cup is further proceeded and supplied into a second sample cup distributor 41 via a second common route 42 and a second sample cup feeder 40. On the other hand, the sample cup from the second analyzing route 39 is also supplied into a second distributor 41 via a second common route 42 and the second sample cup feeder 40 after analysis of the sample starts in the reaction vessel of the second module 32.

In the second distributor 41, it is judged whether the sample is designated to be analyzed by the second module 32 or not. When the sample fed from the first analyzing route 38 is not to be analyzed in the second module 31, the sample cup is fed to a sample receiver 44 right away. When the sample fed from the first analyzing route 38 needs to be further analyzed in the second module 32 the sample cup is returned back to the first sample distributor 37 via a bypass 43 and said first sample feeder 35. By the first distributor 37, the returned sample is supplied into the second analyzing route 39 and the sample contained therein is analyzed in the second module 32.

On the other hand, when the analyzing item of the sample supplied into the second distributor 41 from the second analyzing route 39 is not to be analyzed in the first module 31, the sample cup is supplied into the sample cup receiver 44 right away. But when the sample needs to be further analyzed in the first module 31, the sample cup is returned to the first distributor 37 via the bypass 43 by the second distributor 41, then supplied into the first analyzing route 38 in order to be analyzed by the first module 31. There is provided a CPU 45 by which the function of all devices, i.e. sampler 34, first and second sample feeders 35, 40, first and second sample cup distributors 37, 41, first and second analyzing modules 31, 32, and sample cup receiver 44 are controlled.

The process of the sample of the third embodiment will be explained herein below. It should be noted that the analyzing items of samples No. 1-No. 3 are the same as shown in Table 1.

The sample No. 1 is fed to the common route 36 by the sampler 34 and is then supplied into the first sample cup distributor 37 via the first sample cup feeder 35. The analyzing items of the sample No. 1 are A, C and D which are to be analyzed in the first module 31. Therefore, the first sample cup containing the sample No. 1 is distributed to the first analyzing route 38 by the first distributor 37. The first sample cup is stopped at the sample picking-up position P₁ and a given amount of the sample No. 1 is picked-up and delivered into reaction vessels installed in the first analyzing module 31. During the operation, the second sample cup containing the sample No. 2 is supplied into the first sample cup distributor 37 from the sampler 34. The analyzing items of the sample No. 2 are F and G which are to be analyzed in the second module 32. Therefore the second sample cup is fed to the second analyzing route 39 and positioned at the sample picking-up position P₂ of the second module 32. A predetermined amount of sample No. 2 is picked-up from the sample cup and delivered into reaction vessels in the second analyzing module 32. During the operation, in the first analyzing module 31, the delivery of the sample No. 1 has been finished and the sample cup has been fed to the second sample cup distributor 41. Since the sample No. 1 does not need to be analyzed in the second module 32, the second distributor 41 distributes the sample cup into the sample cup receiver 44 right away via the second sample cup feeder 40 and the second common route 42 During the deliveries of the sample No. 1 in the first analyzing module 31 and the sample No. 2 in the second analyzing module 32, the third sample cup containing the sample No. 3 is supplied into the first sample distributor 37 from the sampler 34. Since the analyzing items of the sample No. 3 are A, B and E, the third sample cup is firstly fed to the first analyzing route 38. After the delivery of sample No. 3 for items A and B has been finished in the first analyzing module 31, the third sample cup is supplied into the second sample distributor 41, and returned to the first sample distributor 37 via the bypass 43 and the first feeder 35 because the analyzing items of the sample No. 3 include the item E. Thereafter, the third sample cup is fed to the second analyzing route 39 for analyzing the item E in the second module 32. After the delivery of the sample No. 3 in the second module 32, the third sample cup is fed to the second sample cup distributor 41 again via the second sample cup feeder 40 and the common route 42. After the delivery of the sample No. 3 has been finished in both the first and second analyzing modules 31 and 32, the third sample cup is fed into the sample cup receiver 44.

Figure 4:
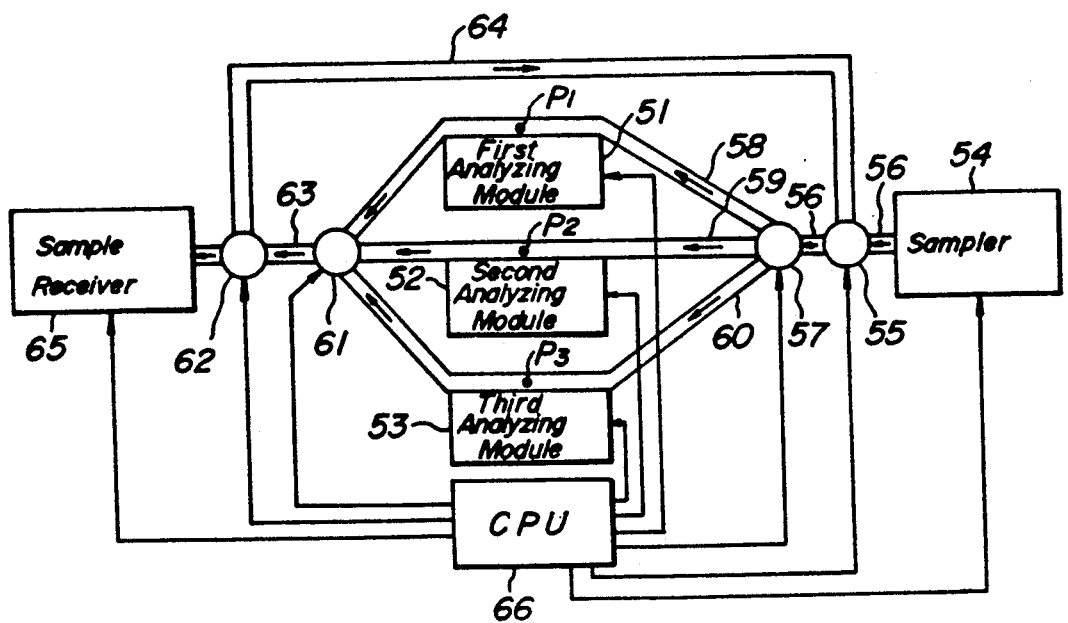
FIG. 4 is a schematic view representing the structure of the fourth embodiment of the automatic analyzing apparatus according to the invention.

FIG. 4 is a schematic view depicting the fourth embodiment of the automatic analyzing apparatus according to the present invention. In the fourth embodiment, there are provided three analyzing modules 51, 52 and 53 in a parallel manner. In the first sample distributor 57, it is possible to distribute the sample cups into either one of the first analyzing route 58, second analyzing route 59 and the third analyzing route 60 in accordance with analyzing items of samples. In this embodiment, since three analyzing modules are arranged, the analyzing items possible to be analyzed in the whole apparatus can be divided into three groups. By selectively distributing the sample cups fed from the first sample cup feeder 55, at which sample cups supplied from the sampler 54 and sample cups returned from the second sample cup distributor 62 via the bypass 64 are fed to the first sample cup distributor 57 one by one, into the first to third analyzing routes 58-60 by the first distributor 57, it is possible to analyze three samples simultaneously, thereby increasing the processing capability of the analyzing apparatus as a whole.

FIG. 5 is a schematic view representing the fifth embodiment of the automatic analyzing apparatus according to the invention. In this embodiment, there are parallely provided three analyzing modules 71, 72, 73 like as the fourth embodiment. But, in the upstream side of analyzing modules, are arranged first and second sample cup distributors 77a, 77b. At the first distributor 77a, an analyzing route is bifurcated into a first analyzing route 78 and a second analyzing route 79a. And the second analyzing route 79a is further biburcated into the extended second analyzing route 79b and a third analyzing route 80 at the second distributor 77b. The sample cups fed from the sample 74 are firstly supplied into the first sample cup distributor 77a. If the sample contained in the sample cup is to be analyzed in the first module 71, the sample cup is fed to the first analyzing route 78, which is connected to the first module 71, and if the sample is not to be analyzed in the first module 71 but should be analyzed in the second or third module 72, 73, the sample cup is fed to the second analyzing route 79a arranged between the first and second distributors 77a and 77b and then supplied into the second distributor 77b. In the second distributor 77b, the sample cups are distributed to the extended second analyzing route 79b, which is connected to the second module 72, or the third analyzing route 80, connected to the third module 73, in accordance with the analyzing items of the sample contained in the sample cup. The numerical number 81 represents a second sample cup feeder by which the sample cups fed from the first and second modules 71, 72 are fed to a third sample cup feeder 82. In the third sample cup feeder 82, the sample cups fed from the third module 73 and from said second feeder 81 are fed to the third sample cup distributor 83 one by one. If the sample supplied into the third distributor 83 needs to be further analyzed in the first, second or third module, the sample cup is returned to the first feeder 75 via a bypass 84. Other sample cups supplied into the third distributor 83 are fed to the sample receiver 85. In such structure of the fifth embodiment of the analyzing apparatus, the sample cups which should be fed to the second and third analyzing modules 72, 73 wait in the second analyzing route 79a arranged between first and second distributors 77a and 77b. Therefore, it is possible to distribute the sample cups into the analyzing modules more effectively.

As stated above in detail, according to the invention, a plurality of analyzing modules are serially or parallely arranged in the analyzing apparatus and there are provided at least two sample cup distributors in the upstream and downstream sides of the analyzing modules. The sample cup is selectively supplied to one of the analyzing modules in accordance with one or more analyzing items of the sample by the distributor arranged in the upstreams side of the modules, and if necessary, the sample cup is returned to the first distributor in order to be analyzed in the other module in an effective manner. Since the distributor does not feed a sample cup to one or more analyzing modules in case the sample does not need to be analyzed by these modules, the processing capability of the analyzing apparatus as a whole is remarkably improved.

In all embodiments mentioned above, the means for conveying the sample cups may be constructed by a known sample cup feeding device such as a conveyor belt, and the sample cup distributor may be formed by the gate mechanism. Further, the analyzing module itself is also well known in the art. Therefore, the detailed construction of the sample cup feeding device, distributor and analyzing module are not explained in this specification.

What is claimed is:

1. An automatic analyzing apparatus comprising:
   sample supply means for successively supplying sample cups containing samples to be analyzed;
   a plurality of analyzing modules, each of which is capable of analyzing at least one test item and has a sample delivery device for delivering samples into reaction vessels;
   a plurality of routes arranged in series with each other where in each intermediate portion of which at least one of said analyzing modules is arranged;
   a plurality of second routes bypassing at least one analyzing module, each of said plurality of second routes is arranged in parallel with a respective one of said first routes; and
   means for controlling the delivery of said sample cups such that each sample cup supplied from said sample cup supply means is selectively delivered into one of said first routes or said second route, at least one of said analyzing modules comprising a plurality of sub-modules and the first route which includes the relevant analyzing module comprises a plurality of sub-routes in each of which is arranged a respective one of said sub-modules.

2. An automatic analyzing apparatus according to claim 1, wherein said plurality of analyzing modules are capable of analyzing completely different test items.

3. An automatic analyzing apparatus according to claim 1, wherein said plurality of analyzing modules are capable of analyzing the same test items.

4. An automatic analyzing apparatus according to claim 1, wherein said plurality of analyzing modules are capable of analyzing partially different test items.

5. An automatic analyzing apparatus comprising:
   sample supply means for successively supplying sample cups containing samples to be analyzed;
   a plurality of analyzing modules, each of which is capable of analyzing at least one analyzing item and has a sample delivery device for delivering samples into reaction vessels;
   a plurality of first routes in each intermediate portion of which at least one of said analyzing modules is arranged, said analyzing modules being arranged in parallel with each other to form a parallel assembly;
   one second route bypassing at said analyzing modules in parallel with said parallel assembly; and
   means for controlling the delivery of said sample cups such that each sample cups supplied from said sample cup supply means are selectively delivered into either one of said first routes or said second route, said controlling means comprising a first sample distributor arranged at a junction point between an introduction side of the parallel assembly of the analyzing modules and the bypass for selectively distributing the sample cups into one of the plurality of first routes, and a second sample cup distributor arranged at a junction point between an exit side of the parallel assembly of the analyzing modules and the bypass for selectively feeding the sample cups into the bypass or a sample cup receiver for receiving the sample cups containing samples which have been delivered into the analyzing modules.

6. An automatic analyzing apparatus according to claim 5, wherein each of said first routes comprises a plurality of sub-routes each arranged between adjacent first routes at their introduction and exit sides, and said controlling means further comprises a plurality of sub-distributors each arranged at junction points of said sub-routes.

7. An automatic analyzing apparatus according to claim 5, wherein said plurality of analyzing modules are capable of analyzing completely different test items.

8. An automatic analyzing apparatus according to claim 5, wherein said plurality of analyzing modules are capable of analyzing the same test items.

9. An automatic analyzing apparatus according to claim 5, wherein said plurality of analyzing modules are capable of analyzing partially different test items.

* * * * *